United States Patent [19]

Ishino et al.

[11] Patent Number: 5,034,566
[45] Date of Patent: Jul. 23, 1991

[54] PROCESS FOR THE PRODUCTION OF 2,3-DIMETHYLBUTENES

[75] Inventors: Masaru Ishino; Michio Yamamoto; Motoo Hazama, all of Osaka, Japan

[73] Assignee: Sumitomo Chemical Company, Limited, Osaka, Japan

[21] Appl. No.: 412,213

[22] Filed: Sep. 25, 1989

[30] Foreign Application Priority Data

Dec. 7, 1988 [JP] Japan .................................. 63-310494

[51] Int. Cl.$^5$ .............................................. C07C 1/00
[52] U.S. Cl. ..................................... 585/641; 585/642
[58] Field of Search ................................. 585/641, 642

[56] References Cited

U.S. PATENT DOCUMENTS 2,404,927  7/1946  Schmerling et al. .
2,613,233 10/1952  Blumer .
3,225,112 12/1965  Hoffman et al. .
3,445,538  5/1969  Kahn .
4,772,695  9/1988  Olofson et al. ..................... 585/642

FOREIGN PATENT DOCUMENTS 0134464  3/1985  European Pat. Off. .
1423174  1/1965  France .

Primary Examiner—Curtis R. Davis
Attorney, Agent, or Firm—Birch, Stewart, Kolasch & Birch

[57] ABSTRACT

In a process for the production of 2,3-dimethylbutenes by the dehydrochlorination of 1-chloro-3,3-dimethylbutane in the presence of a catalyst, a conversion of the starting material and selectivity of the desired product can be improved when at least one compound selected from the group consisting of magnesium compounds, calcium compounds and lanthanum compounds is used as the catalyst.

21 Claims, No Drawings

PROCESS FOR THE PRODUCTION OF 2,3-DIMETHYLBUTENES

BACKGROUND OF THE INVENTION

1. Field of the Invention

The present invention relates to a process for the production of 2,3-dimethylbutenes from 1-chloro-3,3-dimethylbutane through dehydrochlorination.

2. Description of the Related Art 2,3-Dimethylbutenes, that is, 2,3-dimethyl-1-butene and 2,3-dimethyl-2-butene, have been known as raw materials for medicine, agricultural chemicals, perfume and so on.

It is also known that 2,3-dimethylbutenes can be obtained by the dehydrochlorination of 1-chloro-3,3-dimethylbutane in a gas phase in the presence of a catalyst such as silica or alumina (U.S. Pat. No. 2404927) or in a liquid phase in the presence of an alumina catalyst (U.S. Pat. No. 3445538).

However, the known methods have many problems of a low conversion rate or yield, of formation of a large amount of by-products such as methylpentenes, and of unsatisfactory selectivity of the desired product.

SUMMARY OF THE INVENTION

An object of the present invention is to solve the above-mentioned problems.

The present inventors have now found that the problems can be overcome completely by using a certain catalyst.

The present invention provides a process for the production of 2,3-dimethylbutenes by the dehydrochlorination of 1-chloro-3,3-dimethylbutane in the presence of a catalyst, characterized in that at least one compound selected from the group consisting of magnesium compounds, calcium compounds and lanthanum compounds is used as the catalyst.

DETAILED DESCRIPTION OF THE INVENTION

1-Chloro-3,3-dimethylbutane, which is the starting material of the present process, can be easily obtained, for example by the reaction of t-butyl chloride with ethylene in the presence of a catalyst such as aluminum chloride. The starting material may be used even in an unpurified form, unless it contains any impurities such as hydrocarbons and halogenated hydrocarbons which may interfere with the present process.

The catalyst in the present process is selected from the group consisting of magnesium compounds, calcium compounds and lanthanum compounds, such as oxides, halides, hydroxides, sulfates, nitrates, phosphates, carbonates, silicates and borates of magnesium, calcium and lanthanum. Examples of the catalyst are as follows: MgO, CaO, $La_2O_3$, $MgCl_2$, $CaCl_2$, $LaCl_3$, $Mg(OH)_2$, $Ca(OH)_2$, $La(OH)_3$, $MgSO_4$, $CaSO_4$, $La_2(SO_4)_3$, $Mg(NO_3)_2$, $Ca(NO_3)_2$, $La(NO_3)_3$, $Mg_3(PO_4)_2$, $Ca_3(PO_4)_2$, $LaPO_4$, $MgCO_3$, $CaCO_3$, $La_2(CO_3)_3$, $Mg_2SiO_4$, $Ca_2SiO_4$, $La_4(SiO_4)_3$, $MgBO_3$, $CaBO_3$ and $La_2(BO_3)_3$.

As to the magnesium and calcium compounds, the oxide and chloride thereof are preferred. The lanthanum compounds are preferably in the form of the oxide.

Among the magnesium, calcium and lanthanum compounds, the calcium compounds are preferably used.

When the present process is carried out in a gas phase, CaO or $CaCl_2$ is advantageously used. In a liquid phase reaction, $CaCl_2$ is preferred.

The catalysts can be used as such or in a supported form on an inactive material such as an active carbon.

Prior to providing the catalyst, it is usually subjected to calcination at a temperature in the range of from 200 to 600° C. in the air or in an inactive gas atmosphere such as nitrogen under a normal pressure. The calcination of the catalyst can also be performed under a reduced pressure at the same temperature. An anhydrous form of the catalyst can be used without the calcination.

The present process can be carried out in a gas phase or in a liquid phase.

In the gas phase process, the evaporated starting material is passed through a reaction column containing the catalyst at a temperature in the range of from 180 to 400° C., preferably 180 to 350° C. The catalyst can be used as such or in the supported form. The catalyst can be combined with a binder and shaped to a suitable form.

The liquid phase process can be carried out by dispersing the catalyst in the starting material. However, in a preferred emboiment, the catalyst is dispersed in an inactive solvent such as hydrocarbons and halogenated hydrocarbons and then combined with the starting material. When the 2,3-dimethylbutene product is intended to be separated by distillation from the liquid phase, the solvent should have a higher boiling point than both the starting material and the product. Examples of such the high-boiling solvent are mineral oil, liquid paraffin, n-decane, n-tetradecane, n-tridecane, decalin, 1,1,2,2-tetrachloroethane, 1,2,4-trichlorobenzene, 1,2-dichlorobenzene, chlorobenzene and a mixture thereof.

The present liquid phase process can be performed in batch or preferably continuously. In the continuous process, the reaction product can be collected by removing the liquid containing the product from a reactor or by distillating off the product in the form of a gaseous mixture with hydrogen chloride from the liquid phase. In the latter case, 2,3-dimethylbutenes having lower boiling points than the starting material can be preferentially distilled off through a suitable distillation column so as to improve the yield of the product. Further, the ratio of 2,3-dimethyl-1-butene to 2,3-dimethyl-2-butene in the reaction product can be controlled by using a fractionating column.

The liquid phase process can be carried out at a lower temperature at 70 to 300° C., preferably at 100 to 250° C. than the gas phase process.

The present process is usually performed under a pressure of 0.1 to 10 atm. The feed rate of the starting material can vary with the type of the process, the temperature, the pressure and so on. 1-Chloro-3,3-dimethylbutane is usually fed at the rate of 0.01 to 10 kg/hr/kg of the catalyst.

In the present process, the 2,3-dimethylbutene product may react with the hydrogen chloride by-product to form a slight amount of 2-chloro-2,3-dimethylbutane (CDB). CDB can be recovered from the reaction mixture by distillation and recycled by incorporating in the starting material. The formation of CDB can be suppressed by diluting the starting material with a suitable diluent for example a gas such as nitrogen, a rare gas, methane, ethane, propane, ethylene, propylene or butene and an aliphatic or aromatic hydrocarbon such as pentane, hexane, octane, benzene, toluene or xylene. Due to the use of the present catalyst, the diluents even of the aromatic hydrocarbon type hardly react with the starting material or the olefin product, in other words, substantially no alkylated product having a high boiling point is formed.

The hydrogen chloride gas can be removed as a hydrochloric acid after dissolving the gas in water or as a residual gas after the condensation of the gaseous 2,3-dimethylbutene product. The recovered hydrogen chloride can be used in the preparation of t-butyl chloride, which is one of the starting materials for the production of 1-chloro-3,3-dimethylbutane.

The 2,3-dimethylbutene product is usually collected by distillation. It is also possible to fractionate 2,3-dimethyl-1-butene and 2,3-dimethyl-2-butene.

The reaction mixture may contain a small amount of 3,3-dimethyl-1-butene, which can be easily recovered form the mixture by distillation. The by-product can be incorporated in the starting material and then converted to 2,3-dimethylbutenes.

PREFERRED EMBODIMENTS OF THE INVENTION

The present invention is explained more in detail by following Examples. However, the invention is not restricted by the Examples.

Examples 1 to 5 and Comparative Examples 1 to 3

A quartz reaction column having an inner diameter of 10 mm was filled with each 2 cc of the catalysts of 24 to 48 mesh as shown in Table 1. The catalyst was calcined at 250° C. in the air for one hour before the use.

At a flow rate of a nitrogen carrier gas of 100 cc/min, 1-chloro-3,3-dimethylbutane (hereinafter referred to as NHC) was fed at a rate of 2.5 g/hr at 230° C. A gaseous reaction mixture which passed the column was introduced into water and partitioned. An organic phase was subjected to gas chromatography. The results are shown in Table 1.

TABLE 1

| Exam. No. | Catalyst | Temp. (°C.) | Time (hrs) | Conversion (%) | Selectivity (%)[1] | | | | |
|---|---|---|---|---|---|---|---|---|---|
| | | | | | NHE | DMB-1 | DMB-2 | CDB | Rest |
| 1 | CaO | 230 | 5–7 | 92.9 | 2.0 | 23.0 | 64.7 | 3.0 | 7.3 |
| 2 | CaCl$_2$ | 230 | 4–5 | 85.9 | 2.2 | 22.0 | 63.4 | 3.0 | 9.3 |
| 3 | La$_2$O$_3$ | 230 | 4–5 | 79.6 | 2.5 | 23.0 | 66.0 | 1.9 | 6.8 |
| 4 | CaCl$_2$/C[2] | 230 | 4–5 | 86.3 | 5.9 | 23.2 | 64.5 | 1.6 | 4.8 |
| 5 | MgCl$_2$/C[2] | 230 | 4–5 | 87.7 | 4.0 | 24.1 | 63.5 | 1.0 | 7.4 |
| Comp. 1 | Al$_2$O$_3$ | 230 | 2–3 | 21.1 | 7.1 | 21.3 | 57.8 | 2.8 | 10.9 |
| Comp. 2 | Al$_2$O$_3$ | 300 | 1–2 | 56.3 | 4.2 | 20.7 | 46.6 | 5.1 | 23.3 |
| Comp. 3 | SiO$_2$ | 230 | 3–4 | 12.8 | 3.3 | 22.4' | 59.4 | — | 14.6 |

Note:
[1] Composition of the product
NHE: 3,3-dimethyl-1-butene
DMB-1: 2,3-dimethyl-1-butene
DMB-2: 2,3-dimethyl-2-butene
The rest primarily consisted of methylpentenes and hexenes.
[2] CaCl$_2$ and MgCl$_2$ were supported on an active carbon by impregnation in an amount of 20% by weight.

Example 6

The same procedure as in Example 1 was repeated, except that 2 cc of the CaO catalyst was used after the calcination at 400° C. in the air for one hour and that an NHC/n-pentane mixture (weight ratio 50/50) was fed at the rate of 5 g/hr without the carrier gas.
Conversion: 99.0%.
Selectivity: NHE (2.1%), DMB-1 (24.2%), DMB-2 (64.5%), CDB (3.0%), the rest (6.1%).

Example 7

The same procedure as in Example 1 was repeated, except that 4 cc of the CaCl$_2$ catalyst was used after the calcination at 250° C. in the air for one hour and that an NHC/toluene mixture (weight ratio 50/50) was fed at the rate of 10 g/hr with the nitrogen carrier gas at the flow rate of 5 cc/min at various temperatures in the range of from 180 to 300° C. The results are shown in Table 2.

A high-boiling compound such as alkylated toluene was never formed.

TABLE 2

| Temp. (°C.) | Time (hrs) | Conversion (%) | Selectivity (%) | | | | |
|---|---|---|---|---|---|---|---|
| | | | NHE | DMB-1 | DMB-2 | CDB | Rest |
| 180 | 3–4 | 89.8 | 1.5 | 16.1 | 59.8 | 16.0 | 6.6 |
| 200 | 7–8 | 96.0 | 1.7 | 18.9 | 63.2 | 10.3 | 5.9 |
| 260 | 11–12 | 99.9 | 2.2 | 23.6 | 62.9 | 6.2 | 5.0 |
| 300 | 15–16 | 100 | 2.4 | 26.3 | 60.5 | 5.1 | 5.7 |

Example 8

The same procedure as in Example 1 was repeated, except that 4 cc of the CaCl$_2$ catalyst was used and that NHC was fed at the rate of 6.1 g/hr at 240° C. without the carrier gas.
Conversion: 99.2%.
Selectivity: NHE (2.5%), DMB-1 (26.0%), DMB-2 (64.1%), CDB (2.7%), the rest (4.7%).

Example 9

A quartz reaction column having the inner diameter of 18 mm was filled with 10 cc of the CaO catalyst of 24 to 48 mesh. The catalyst was calcined at 400° C. in the air for one hour before the use.

With flowing the nitrogen gas at the flow rate of 400 cc/min, NHC was fed at the rate of 12.0 g/hr at 220° C. The conversion and the selectivity were determined with time. The results are shown in Table 3.

TABLE 3

| Time (hrs) | Conversion (%) | Selectivity (%) | | | | |
|---|---|---|---|---|---|---|
| | | NHE | DMB-1 | DMB-2 | CDB | Rest |
| 4–9 | 98.1 | 2.2 | 23.1 | 68.0 | 0.9 | 5.8 |
| 51–58 | 93.6 | 2.7 | 23.4 | 67.5 | 0.9 | 5.5 |

Example 10 and Comparative Example 4

In a simple distillation unit consisting of a 100 cc four necked flask with a magnetic stirrer, a thermometer, a starting-material inlet and a gas outlet, the catalyst in a powder form (12 g) was dispersed in a liquid paraffin (30 g) by stirring and then heated at various temperatures as shown in Table 4. Then, NHC was continuously fed into the flask at the rate of 2.5 g/hr.

The gaseous mixture of the desired product with gaseous hydrogen chloride was distilled off, introduced into water and partitioned. An organic phase was subjected to gas chromatography. The results in a steady state when the amount of the distillate including HCl as almost equal to that of the feed are shown in Table 4.

TABLE 4

| Exam. No. | Catalyst | Temp. (°C.) | Time (hrs) | Conversion (%) | Selectivity (%) | | | | |
|---|---|---|---|---|---|---|---|---|---|
| | | | | | NHE | DMB-1 | DMB-2 | CDB | Rest |
| 10 | CaCl$_2$* | 230 | 5–6 | 93.7 | 2.0 | 22.7 | 51.1 | 2.1 | 22.1 |
| | | 170 | 5–6 | 95.3 | 2.0 | 23.9 | 58.2 | 4.7 | 11.2 |
| | | 150 | 5–6 | 98.4 | 1.8 | 25.8 | 64.4 | 1.9 | 6.1 |
| | | 130 | 6–7 | 98.6 | 2.4 | 27.2 | 66.9 | 1.0 | 2.5 |
| Comp. 4 | Al$_2$O$_3$* | 230 | 5–7 | 52.7 | 3.0 | 19.9 | 44.6 | 23.1 | 9.4 |
| | | 170 | 5–7 | <4 | — | — | — | — | — |

Note:
*CaCl$_2$ or Al(OH)$_3$ was calcined at 200° C. or 250° C., respectively in a nitrogen atmosphere for one hour before the use.

Example 11

The same procedure as in Example 10 was repeated at 170° C. The distillate was analyzed with time. The results are shown in Table 5.

TABLE 5

| Time (hrs) | Conversion (%) | Selectivity (%) | | | | |
|---|---|---|---|---|---|---|
| | | NHE | DMB-1 | DMB-2 | CDB | Rest |
| 63–65 | 95.8 | 3.5 | 34.8 | 55.9 | 1.4 | 4.4 |
| 117–119 | 95.0 | 4.1 | 37.3 | 54.2 | 0.8 | 3.6 |
| 154–156 | 95.6 | 4.0 | 34.2 | 56.6 | 1.1 | 4.1 |

Example 12

Into a 50 cc four necked glass flask equipped with a magnetic stirrer, a thermometer, a starting-material inlet and a simple fractionating column (inner diameter: 10 mm, length: 150 mm) containing glass packing, the CaCl$_2$ catalyst (5 g) and liquid paraffin (20 g) were introduced. The catalyst was dehydrated at 200° C. under a nitrogen atmosphere before the use. NHC was fed at the rate of 2.5 g/hr at 180° C. The distillation temperature was controlled by heating outside the fractionating column.

The results in a steady state are shown in Table 6.

TABLE 6

| Distillation Temp. (°C.) | Time (hrs) | Conversion (%) | Selectivity (%) | | | | |
|---|---|---|---|---|---|---|---|
| | | | NHE | DMB-1 | DMB-2 | CDB | Rest |
| 60 | 31–33 | 91.6 | 2.4 | 19.2 | 59.6 | 13.9 | 4.9 |
| 50 | 24–26 | 97.9 | 2.6 | 22.8 | 63.6 | 6.3 | 4.7 |
| 40 | 45–47 | 99.7 | 4.4 | 49.9 | 35.8 | 6.2 | 3.7 |

Examples 13 and 14

Into a 50 cc four necked flask equipped with a magnetic stirrer, a thermometer, a starting-material inlet and an outlet, the anhydrous CaCl$_2$ catalyst (5 g) and decalin or o-dichlorobenzen (20 ml) as a solvent were introduced.

The same procedure as in Example 10 was repeated by feeding NHC at the rate of 2.5 g/hr at the reaction temperature of 170°) C.

The results in a steady state are shown in Table 7.

TABLE 7

| Exam. No. | Solvent | Time (hrs) | Conversion (%) | Selectivity (%) | | | | |
|---|---|---|---|---|---|---|---|---|
| | | | | NHE | DMB-1 | DMB-2 | CDB | Rest |
| 13 | decalin | 7–9 | 92.0 | 1.9 | 19.9 | 63.0 | 5.8 | 9.4 |
| 14 | o-dichlorobenzene | 7–9 | 95.0 | 1.6 | 18.9 | 61.7 | 3.5 | 14.3 |

Example 15

Into the same reaction unit as in Example 13, CaCl$_2$ (10 g) and NHC (20 ml) were introduced. The outlet was equipped with a condenser. The distillation temperature was controlled in the range of from 40 to 50° C. The flask was placed in an oil bath at 130° C. The reaction mixture was circulated at the rate of 2.5 g NHC/hr by a pump.

The results in a steady state (15 to 17 hours from the beginning of the reaction) are as follows:
Reaction temperature in the flask: 113 to 115° C.
Conversion: 99.9%
Selectivity: NHE (1.9%), DMB-1 (34.6%), DMB-2 (62.0%), CDB (0.9%), the rest (0.6%)

Examples 16 and 17 and Comparative Example 5

In the same procedure as in Example 10, the catalyst (4 g) and liquid paraffin (20 g) were introduced into the flask. Then, at the flow rate of the nitrogen gas of 120 cc/min, NHC was fed at the rate of 5.8 g/hr at 230° C.

The results after 4 to 5 hours from the beginning of the reaction are shown in Table 8.

TABLE 8

| Exam. No. | Catalyst* | Conversion (%) | Selectivity (%) | | | | |
|---|---|---|---|---|---|---|---|
| | | | NHE | DMB-1 | DMB-2 | CDB | Rest |
| 16 | CaO | 77.6 | 1.3 | 17.7 | 49.7 | 22.0 | 9.3 |
| 17 | La$_2$O$_3$ | 83.7 | 1.8 | 17.5 | 51.2 | 20.6 | 8.9 |
| Comp. 5 | Al$_2$O$_3$ | 49.3 | 2.0 | 15.4 | 44.0 | 24.7 | 13.9 |

*The catalysts (CaO, La$_2$O$_3$ or Al(OH)$_3$) were calcined at 250° C. in a nitrogen atmosphere for one hour before the use.

What is claimed is:

1. A process for the production of 2,3-dimethylbutenes by the dehydrochlorination of 1-chloro-3,3-dimethylbutane in the presence of a catalyst, characterized in that at least one compound selected from the group consisting of magnesium compounds, calcium compounds and lanthanum compounds is used as the catalyst.

2. The process of claim 1, wherein calcium oxide or chloride is used as the catalyst.

3. The process of claim 1, wherein magnesium oxide or chloride is used as the catalyst.

4. The process of claim 1, wherein lanthanum oxide is used as the catalyst.

5. The process of claim 1, which is a gas phase reaction.

6. The process of claim 5, wherein calcium oxide or chloride is used as the catalyst.

7. The process of claim 5, wherein the reaction temperature is in the range of from 180 to 400° C.

8. The process of claim 7, wherein the reaction temperature is in the range of from 180 to 350° C.

9. The process of claim 1, which is a liquid phase reaction.

10. The process of claim 9, wherein calcium chloride is used as the catalyst.

11. The process of claim 9, wherein the reaction temperature is in the range of from 70 to 300° C.

12. The process of claim 11, wherein the reaction temperature is in the range of from 100 to 250° C.

13. A process for the production of 2,3-dimethylbutenes by the dehydrochlorination of 1-chloro-3,3-dimethylbutane in the presence of catalyst, wherein the catalyst is selected from the group consisting of calcium oxide and calcium chloride.

14. A process for the production of 2,3-dimethylbutenes by the dehydrochlorination of 1-chloro-3,3-dimethylbutane in the presence of a catalyst, wherein the catalyst is selected from the group consisting of magnesium oxide and magnesium chloride.

15. A process for the production of 2,3-dimethylbutenes by the dehydrochlorination of 1-chloro-3,3-dimethylbutane in the presence of a catalyst, wherein the catalyst is lanthanum oxide.

16. The process of any of claims 13-15, which is a gas phase reaction.

17. The process of claim 16, wherein the reaction temperature is in the range of from 180 to 400° C.

18. The process of claim 11, wherein the reaction temperature is in the range of from 180 to 350° C.

19. The process of any of claims 13-15, which is a liquid phase reaction.

20. The process of claim 19, wherein the reaction temperature is in the range of from 70 to 300° C.

21. The process of claim 20, wherein the reaction temperature is in the range of from 100 to 250° C.

* * * * *